United States Patent
Inoue (10) Patent No.: US 8,430,821 B2
(45) Date of Patent: Apr. 30, 2013

(54) BLOOD PRESSURE MEASURING APPARATUS

(75) Inventor: Kouichi Inoue, Ashigarakami-gun (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 295 days.

(21) Appl. No.: 12/844,207

(22) Filed: Jul. 27, 2010

(65) Prior Publication Data

US 2010/0292587 A1    Nov. 18, 2010

Related U.S. Application Data

(63) Continuation of application No. PCT/JP2009/050738, filed on Jan. 20, 2009.

(30) Foreign Application Priority Data

Jan. 29, 2008    (JP) ................. 2008-018021

(51) Int. Cl.
    *A61B 5/02*    (2006.01)
(52) U.S. Cl.
    USPC ............. 600/499; 600/490; 600/492
(58) Field of Classification Search ........... 600/499
    See application file for complete search history.

(56) References Cited

U.S. PATENT DOCUMENTS

| | | | |
|---|---|---|---|
| 6,969,356 B2 * | 11/2005 | Nishibayashi | 600/499 |
| 7,070,567 B2 * | 7/2006 | Mizukoshi et al. | 600/499 |
| 2005/0015015 A1 | 1/2005 | Mizukoshi et al. | |
| 2009/0312651 A1 | 12/2009 | Sano et al. | |

FOREIGN PATENT DOCUMENTS

| | | |
|---|---|---|
| JP | 63-150051 A | 6/1988 |
| JP | 3667326 B2 | 7/2005 |
| JP | 2007-125247 A | 5/2007 |
| JP | 2007-167171 | 7/2007 |
| JP | 2008-005926 A | 1/2008 |
| JP | 2008-005927 A | 1/2008 |

OTHER PUBLICATIONS

Taiwanese Office Action dated Dec. 7, 2011, issued in the corresponding Taiwanese Patent Application No. 098102688 (6 pages).
International Search Report (PCT/ISA/210) issued on Feb. 5, 2009, by Japanese Patent Office as the International Searching Authority for International Application No. PCT/JP2009/050738.
Written Opinion (PCT/ISA/237) issued on Feb. 5, 2009, by Japanese Patent Office as the International Searching Authority for International Application No. PCT/JP2009/050738.

* cited by examiner

*Primary Examiner* — Patricia Mallari
*Assistant Examiner* — Mitchell Alter
(74) *Attorney, Agent, or Firm* — Buchanan Ingersoll & Rooney PC (57) ABSTRACT

A blood pressure measuring apparatus includes a cuff member (2) which can be attached to and detached from a blood pressure measurement portion, and a cuff main body (1) including a compression air bladder (8) for pressing the blood pressure measurement portion, a sub air bladder (7), and a pulse wave detection air bladder (5). After pressurization is performed by compression air bladder pressurizing/depressurizing means (22, 23) and sub air bladder pressurizing/depressurizing means (27, 26), depressurization is controlled at the same depressurization rate, thereby reducing the cuff-edge effect and obtaining a pulse wave signal.

6 Claims, 4 Drawing Sheets

PULSE WAVE M PRODUCED BY BLOOD FLOW IN CUFF DOWNSTREAM SIDE

BLOOD PRESSURE MEASURING APPARATUS

TECHNICAL FIELD

The present invention relates to a blood pressure measuring apparatus and, more particularly, to a technique of measuring the blood pressure by the oscillometric method.

BACKGROUND ART

The following method is generally used when obtaining the systolic blood pressure by a blood pressure measuring method using a compression air bladder. That is, the blood flow in an artery is stopped by raising the internal pressure of the compression air bladder such that the internal pressure is equal to or higher than the systolic blood pressure as the peak pressure of the intra-arterial pressure. After that, the internal pressure of the compression air bladder is gradually lowered, and a phenomenon in which the blood reflows when the systolic blood pressure matches the pressure of the compression air bladder is detected.

A blood pressure measuring apparatus using the Korotkoff method (auditory method) presently widely adopted as a method of detecting this blood reflow, the blood flow is stopped by making the internal pressure of the compression air bladder equal to or higher than the systolic blood pressure, and the pressure of the compression air bladder is gradually lowered. Korotkoff sounds (K sounds) generated at the timing at which the blood flow once stopped reflows are detected in a peripheral portion on the downstream side of the compression air bladder or a cuff. The internal pressure of the compression air bladder at the same timing is obtained as a systolic blood pressure value.

On the other hand, in an oscillometric-type blood pressure measuring apparatus, the internal pressure of the compression air bladder is once raised to a high pressure equal to or higher than the systolic blood pressure as in the Korotkoff method (auscultatory method) described above, but the occurrence of a blood flow to the cuff downstream side cannot clearly be detected. Instead, therefore, the vibration of the compression air bladder based on the change in volume of the artery, which occurs when the internal pressure of the air bladder is gradually lowered, is detected. The blood pressure is determined by the profile of the change in amplitude of this vibration.

The above-mentioned, oscillometric-type blood pressure measuring apparatus is designed to obtain a blood pressure value from the vibration of the air bladder by the profile of the change in internal pressure of the air bladder. This obviates the need for a microphone or stethoscope for detecting the Korotkoff sounds, which is essential in the Korotkoff method. Accordingly, the oscillometric-type blood pressure measuring apparatus has the advantages that the number of parts can be made smaller than that of the Korotkoff method, and the manufacturing cost can be decreased because an electronic circuit for detecting the K sounds (Korotkoff sounds) can be omitted.

In addition, the Korotkoff-type blood pressure measuring apparatus is readily influenced by noise caused by the frictional sound of cuff cloth or a cuff tube generated during measurement, and external noise such as the noise of an air-conditioning apparatus or human voices. Even when using the frequency discrimination method, the Korotkoff-type blood pressure measuring apparatus is still weak against these noises because the frequency components of the noises are close to those of the Korotkoff sounds.

On the other hand, the frequency components of the pressure fluctuation used in the oscillometric-type blood pressure measuring apparatus are lower than those of the Korotkoff sounds and largely dissociated from the frequencies of the external noise. Therefore, the oscillometric-type blood pressure measuring apparatus is not easily influenced by noise.

Unfortunately, even the oscillometric method has a drawback: the oscillometric-type blood pressure measuring apparatus has a problem pertaining to the detection of the systolic blood pressure, which is caused by the blood vessel pressing characteristic of the compression air bladder or cuff. When pressing the artery of the upper arm as a measurement portion by winding the built-in compression air bladder of the cuff around the upper arm and inflating the compression air bladder, the force of pressing the upper arm generated when the compression air bladder is inflated reflects the internal pressure of the air bladder in a central portion in the widthwise direction (the longitudinal direction of the upper arm) of the air bladder. However, this pressing force reflecting the internal pressure of the air bladder cannot be obtained in the two end portions spaced apart from the central portion and extending along the longitudinal direction of the upper arm. That is, the compression air bladder has the pressing characteristic called a cuff-edge effect that the pressing force gradually reduces from the central portion in the widthwise direction of the air bladder toward the two end portions of the air bladder.

Due to this pressing characteristic, when the cuff internal pressure (the internal pressure of the air bladder) is made equal to or higher than the systolic blood pressure to occlude the blood flow in a measurement portion and then gradually reduced, the blood flow is occluded in only the central portion of the compression air bladder or cuff at the timing at which the cuff internal pressure is slightly higher than the systolic blood pressure. Consequently, the blood flows into the space between the upstream portion and central portion of the cuff in synchronism with the heart beat, and the internal volume of the cuff changes. At the timing at which the cuff internal pressure is higher than the systolic blood pressure, therefore, the change in pulse wave (the increase in amplitude) caused by the change in internal volume of the cuff is detected. This makes it impossible to detect the timing at which the cuff internal pressure becomes lower than the systolic blood pressure (the change in internal volume of the cuff that is an index for the detection of the blood flow occurring downstream of the cuff). This poses the problem that the systolic blood pressure cannot accurately be measured.

Accordingly, the double-cuff method has been proposed to solve the above-mentioned problem in the detection of the blood reflow phenomenon.

This double-cuff method uses a compression air bladder for pressing the blood vessel, and a pulse wave detection air bladder that is separated from the compression function and detects only a pulse wave generated by blood reflow slightly downstream of a central portion below the compression air bladder, thereby reducing the above-mentioned influence of a pulse wave, which is the problem of the oscillometric method, based on the volume change on the upstream side of the compression air bladder when measuring the systolic blood pressure. This makes it possible to detect, at a high S/N ratio, the volume change on the downstream side of the compression air bladder as an index for the determination of the systolic blood pressure.

Unfortunately, at the systolic blood pressure detection timing at which the cuff pressure of the compression air bladder is almost equal to the systolic blood pressure, a blood flow entering the upstream side below the compression air bladder enters the vicinity of the central portion of the compression air bladder, that is, comes very close to the pulse wave detection air bladder. Vibrations caused by this entry are partially transmitted to the pulse wave detection air bladder via a living body. Also, since the pulse wave detection air bladder is formed below the compression air bladder, cuff vibrations based on the volume change of the compression air bladder, which is detected by the compression air bladder, are partially transmitted to the pulse wave detection air bladder. This causes a phenomenon in which the S/N ratio of the systolic blood pressure measurement decreases.

Accordingly, the following proposals have been made in order to prevent the pulse wave detection air bladder from detecting the pulse wave generated by the blood flow entering the upstream side, that is, to prevent the blood flow entering from the cuff upstream side, when the blood vessel is closed with pressure by the compression air bladder, from approaching the pulse wave detection air bladder, by broadening the range within which the blood vessel is closed with pressure. That is, a backing for improving the pressing performance of the pulse wave detection air bladder is installed, a damper for damping the pulse wave transmitted from the compression air bladder is installed between the pulse wave detection air bladder and compression air bladder, and a damper for damping the pulse wave on the upstream side below the compression air bladder is installed (Japanese Patent No. 3667326).

These proposals can increase the pressing force of the pulse wave detection air bladder. However, there are large variations in distance at which the position where the pulse wave enters from the upstream portion of the cuff at the end of the air bladder is spaced apart from the pulse wave detection air bladder. Also, if the distance is short, the pulse wave detection air bladder may detect the upstream pulse wave. Furthermore, the damping characteristic concerning the frequency of a member to be used is limited: it is possible to damp relatively high frequency components of the pulse wave, but it is impossible to sufficiently damp low frequency components. This sometimes makes it impossible to detect the systolic blood pressure at a high S/N ratio.

To solve this problem, it is possible to improve the performance of the damper for damping the pulse wave on the upstream side below the compression air bladder. However, if a cover-like rigid material is used as the damper in order to improve the damping performance, the damper itself inhibits the compression air bladder from pressing an arm especially when the diameter of the arm is small. This produces dissociation between the internal pressure of the compression air bladder and the actual pressure pressing the upper arm. Consequently, there is no means for obtaining the pressure pressing the upper arm at the blood reflow timing. Also, a generally used compressive damping material such as foamed urethane has the drawback that the degree of compression of the damping material changes in accordance with the pressure of the compression air bladder and this changes the damping characteristic. Over the whole pressure range, therefore, the settings of the damper required to fully utilize the damping performance change each time in accordance the shape of an arm and the way the compression air bladder is wound. This makes it difficult for the conventionally proposed methods to prevent a damper having a satisfactory damping performance from inhibiting the compression air bladder from pressing the arm of any person.

Furthermore, as a technique that detects, with high sensitivity, the blood flowing toward the peripheral side of a cuff when the cuff pressure becomes lower than the systolic blood pressure in an oscillometric-type sphygmomanometer, an arrangement has been proposed in which a pulse wave detection air bladder is formed downstream of a cuff so as to increase the sensitivity of detection of a pulse wave on the cuff peripheral side and detect a pulse wave on the cuff downstream side, and a compression air bladder for pressing a whole blood pressure measurement portion is connected to the pulse wave detection air bladder (Japanese Patent Laid-Open No. 63-150051).

Unfortunately, each arrangement described above has a connecting portion for connecting the blood blocking bladder and air bladder. Accordingly, the upstream-side pulse wave is detected as it is superposed on the downstream-side pulse wave. This makes it impossible to increase the S/N ratio for the detection of the systolic blood pressure.

DISCLOSURE OF INVENTION

The present invention, therefore, has been made in consideration of the above situation, and has as its object to provide a blood pressure measuring apparatus capable of setting a compression air bladder and sub air bladder at the same depressurization rate, and obtaining, regardless of the way a cuff is wound, the effect of sufficiently suppressing the cuff-edge effect over the whole pressure range within which the compression air bladder presses an arm, thereby clearly detecting a pulse wave generated by the blood flowing toward the cuff downstream side, which is an index for the measurement of the systolic blood pressure (a change in pulse wave at the cuff pressure detection timing, which represents the systolic blood pressure), and damping an extra pulse wave signal superposed on this pulse wave and detected upstream of the compression air bladder.

To solve the above problems, a blood pressure measuring apparatus according to the present invention comprises a cuff member configured to be attached to and detached from a blood pressure measurement portion, a cuff main body including a compression air bladder which is formed on a side of the cuff member, which is in contact with the blood pressure measurement portion, and presses the blood pressure measurement portion, a sub air bladder which is formed on a side of the compression air bladder, which is in contact with the blood pressure measurement portion, and presses a heart side of the blood pressure measurement portion, and a pulse wave detection air bladder which is formed on the side of the compression air bladder, which is in contact with the blood pressure measurement portion, and detects a pulse wave downstream of a central portion of the blood pressure measurement portion, a compression air bladder pressurizing/depressurizing unit configured to pressurize/depressurize the compression air bladder and the pulse wave detection air bladder, a sub air bladder pressurizing/depressurizing unit configured to pressurize/depressurize the sub air bladder, a cuff pressure detecting unit configured to obtain a cuff pressure signal from the pulse wave detection air bladder, a sub air bladder pressure detecting unit configured to obtain a sub air bladder pressure signal from the sub air bladder, a pulse wave detecting unit configured to detect a pulse wave superposed on the cuff pressure signal, and obtaining a pulse wave signal, a blood pressure determining unit configured to determine a blood pressure value based on the cuff pressure signal and the pulse wave signal, a blood pressure display unit configured to display the blood pressure value, a first tube connected between the pulse wave detection air bladder and the cuff pressure detecting unit, a second tube connected between the compression air bladder and the compression air bladder pressurizing/depressurizing unit, and connected to the cuff pressure detecting unit via a fluid resistance, and a third tube connected between the sub air bladder and the sub air bladder pressurizing/depressurizing unit, and connected to the sub air bladder and the sub air bladder pressurizing/depressurizing unit, wherein after the compression air bladder and the sub air bladder are pressurized by the compression air bladder pressurizing/depressurizing unit and the sub air bladder pressurizing/depressurizing unit, the compression air bladder pressurizing/depressurizing unit and the sub air bladder pressurizing/depressurizing unit are controlled to depressurize the compression air bladder and the sub air bladder at the same depressurization rate, thereby obtaining the pulse wave signal.

The blood pressure measuring apparatus further comprises control of pressurizing the sub air bladder to a prescribed pressure by the sub air bladder pressurizing/depressurizing unit, and then stopping the pressurization, pressurizing the compression air bladder to a pressurization target pressure higher than a systolic blood pressure by the compression air bladder pressurizing/depressurizing unit, and then stopping the pressurization, and determining whether the prescribed pressure of the sub air bladder differs from the pressurization target pressure, and, if the prescribed pressure differs from the pressurization target pressure, making the prescribed pressure equal to the pressurization target pressure by the sub air bladder pressurizing/depressurizing unit.

The blood pressure measuring apparatus further comprises control of pressurizing the sub air bladder by the sub air bladder pressurizing/depressurizing unit, and stopping the pressurization after an elapse of a prescribed time, pressurizing the compression air bladder to a pressurization target pressure higher than a systolic blood pressure by the compression air bladder pressurizing/depressurizing unit, and then stopping the pressurization, and determining whether the pressure of the sub air bladder differs from the pressurization target pressure, and, if the pressure of the sub air bladder differs from the pressurization target pressure, making the prescribed pressure of the sub air bladder equal to the pressurization target pressure by the sub air bladder pressurizing/depressurizing unit.

The blood pressure measuring apparatus further comprises control of pressurizing the sub air bladder by the sub air bladder pressurizing/depressurizing unit, and stopping the pressurization after an elapse of a prescribed time, pressurizing the compression air bladder to a pressurization target pressure higher than a systolic blood pressure by the compression air bladder pressurizing/depressurizing unit, and then stopping the pressurization, and determining whether the prescribed pressure of the sub air bladder differs from the pressurization target pressure, and, if the prescribed pressure differs from the pressurization target pressure, making the prescribed pressure equal to the pressurization target pressure by the sub air bladder pressurizing/depressurizing unit.

The blood pressure measuring apparatus further comprises control of simultaneously starting pressurization by the compression air bladder pressurizing/depressurizing unit and the sub air bladder pressurizing/depressurizing unit, and stopping the sub air bladder pressurizing/depressurizing unit when the sub air bladder has reached a prescribed time, pressurizing the compression air bladder to a pressurization target pressure higher than a systolic blood pressure by the compression air bladder pressurizing/depressurizing unit, and then stopping the pressurization, and determining whether the pressure of the sub air bladder differs from the pressurization target pressure, and, if the pressure of the sub air bladder differs from the pressurization target pressure, making the pressure of the sub air bladder equal to the pressurization target pressure by the sub air bladder pressurizing/depressurizing unit.

The blood pressure measuring apparatus, wherein the sub air bladder pressurizing/depressurizing unit performs control to cancel a pulse wave based on a blood vessel volume change detected from the pressure signal of the sub air bladder, thereby attenuating a pulse wave signal detected upstream of the pulse wave detection air bladder.

Other features of the present invention will be apparent from the following best mode for carrying out the invention and the accompanying drawings. Note that the same reference numerals denote the same or similar parts in the accompanying drawings.

BRIEF DESCRIPTION OF DRAWINGS

The accompanying drawings, which are incorporated in and constitute a part of the specification, illustrate an embodiment of the invention and, together with the description, serve to explain the principle of the invention.

EXPLANATION OF REFERENCE NUMERALS

1 . . . cuff main body
2 . . . cuff member
5 . . . pulse wave detection air bladder
7 . . . sub air bladder
8 . . . compression air bladder
11 . . . first tube
12 . . . second tube
13 . . . third tube
14 . . . fluid resistor
22 . . . rapid exhaust valve/constant-rate exhaust valve (for compression air bladder and pulse wave detection air bladder)
23 . . . pump (pressurizing/depressurizing unit of compression air bladder and pulse wave detection air bladder)
26 . . . rapid exhaust valve/constant-rate exhaust valve (for sub air bladder)
27 . . . pump (pressurizing/depressurizing unit of sub air bladder)
31 . . . pressure sensor (cuff pressure detecting unit)
16 . . . pressure sensor (sub air bladder pressure detecting unit)
H . . . heart
K . . . artery

BEST MODE FOR CARRYING OUT THE INVENTION

Figure 1:
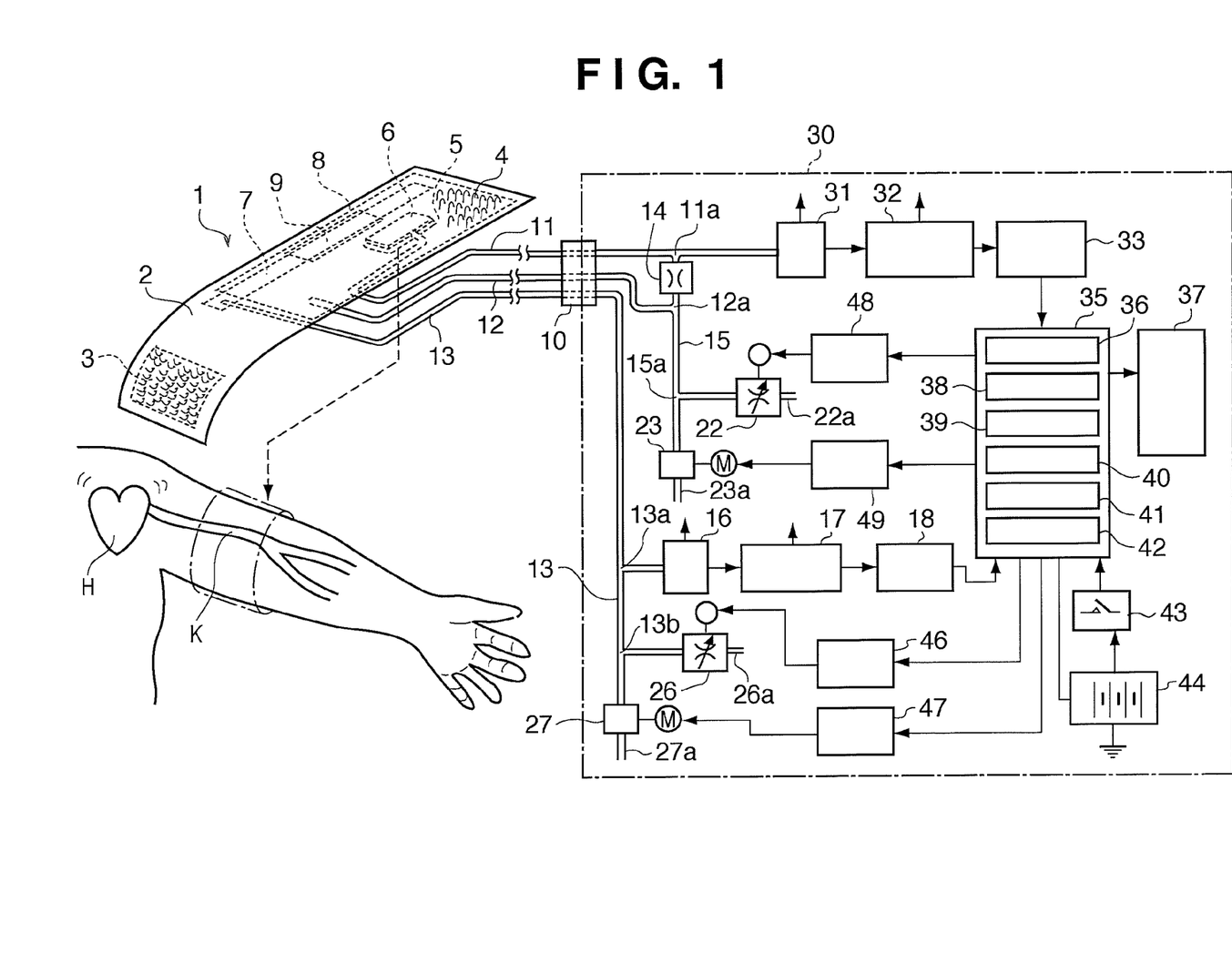
FIG. 1 is a block diagram of a blood pressure measuring apparatus according to an embodiment of the present invention.

An embodiment of the present invention will be explained below with reference to the accompanying drawings. FIG. 1 is a block diagram showing a blood pressure measuring apparatus of the embodiment of the present invention.

In this embodiment shown in FIG. 1, a cuff main body 1 includes a cloth cuff member 2 that can be attached to and detached from a blood pressure measurement portion including the upper arm. The end portion of the rear surface of the cuff member 2 has a male hook-and-loop fastener 3 indicated by broken lines. The end portion of the front surface of the cuff member 2 has a female hook-and-loop fastener 4.

The cuff main body 1 can be attached by winding the cuff member 2 around the upper arm as shown in FIG. 1, and locking the hook-and-loop fasteners. The hook-and-loop fasteners described above are merely examples, and other members may be used. It is also possible to use a cylindrical arm-in cuff member into which the upper arm is inserted.

A compression air bladder 8 indicated by broken lines is formed inside the cuff member 2, in order to press a whole blood pressure measurement portion. A sub air bladder 7 indicated by broken lines is formed on the side of the compression air bladder 8, which is in contact with the blood pressure measurement portion. The sub air bladder 7 has a small width in order to press the side of the blood pressure measurement portion, which is close to a heart H. A first damping member 9 indicated by broken lines is formed between the sub air bladder 7 and compression air bladder 8, and damps the vibration of the sub air bladder 7.

Also, a pulse wave detection air bladder 5 indicated by broken lines is formed on the side of the compression air bladder 8 which is brought into contact with a blood pressure measurement portion (living body). The pulse wave detection air bladder 5 presses a slightly downstream side of the blood pressure measurement portion, and detects a pulse wave on the slightly downstream side. The pulse wave detection air bladder 5 is fixed to the cuff main body 1 with a second damping member 6 being interposed between them.

To pressurize and depressurize the cuff main body 1, the compression air bladder 8 is connected to a second tube 12 and tube 15. The pulse wave detection air bladder 5 is connected to a first tube 11. A fluid resistor 14 is connected between a branched portion 11a of the first tube 11 and a branched portion 12a of the second tube 12. The tube 15 is connected to the branched portion 12a. A rapid exhaust valve/constant-rate exhaust valve 22 is connected to a branched portion 15a of the tube 15. A pump 23 as a pressurizing unit is connected to the tube 15.

A pressure sensor 31 as a cuff pressure detecting unit configured to obtain a cuff pressure signal from the change in pressure of the pulse wave detection air bladder 5 is connected to the pulse wave detection air bladder 5 via the first tube 11. A third tube 13 connects the sub air bladder 7 to a pump 27 as a pressurizing means of a sub air bladder pressurizing/depressurizing means. A pressure sensor 16 as a sub air bladder pressure detecting unit configured to obtain the internal pressure of the sub air bladder 7 is connected to a branched portion 13a of the third tube 13 connected to the sub air bladder 7.

The first, second, and third tubes 11, 12, and 13 are made of soft tubes, and attachable to and detachable from a main body 30 via a connector 10. The pump 27 is connected to the upstream side of the third tube 13, and a rapid exhaust valve/constant-rate exhaust valve 26 is connected to a branched portion 13b.

The rapid exhaust valve/constant-rate exhaust valve 22 is connected to a controller 48, and the rapid exhaust valve/constant-rate exhaust valve 26 is connected to a controller 46. The opening degree of the opening area of the orifice of a solenoid valve of each of the rapid exhaust valve/constant-rate exhaust valve 22 and rapid exhaust valve/constant-rate exhaust valve 26 can be controlled in accordance with a command from a central controller 35.

Motors M are the power sources of the pumps 23 and 27. When driven by power supply from pump drivers 49 and 47, the motors M supply the external air into these pumps through openings 23a and 27a. Pressurization is performed by the air thus supplied: pressurization can be performed by supplying the pressurizing air to the air bladders via the branched portion 15a and third tube 13 described above.

The rapid exhaust valve/constant-rate exhaust valve 22 described above is designed to change the opening area by changing the magnitude of the electromagnetic force, so as to perform depressurization at a depressurization rate of 2 to 4 mmHg/sec. Therefore, an arbitrary depressurization rate can be set by obtaining a PWM (pulse width modulation) driving signal from the controller 48. Similarly, the rapid exhaust valve/constant-rate exhaust valve 26 has a structure that changes the opening area by the magnitude of the electromagnetic force so that the pressures of the compression air bladder 8 and sub air bladder 7 are constant. The pressure of the sub air bladder 7 can be controlled by obtaining a PWM driving signal from the controller 46.

On the other hand, the pressure sensor 31 as an air bladder pressure detecting unit receives a compressive pressure signal from the compression air bladder 8, in which the pulse wave component is attenuated by the fluid resistor 14 described above, and the pressure change of the pulse wave detection air bladder 5. A pressure controller 32 for conversion into an analog electrical signal is connected to the pressure sensor 31, and an A/D converter 33 is connected to the pressure controller 32. The A/D converter 33 converts an analog signal into a digital signal, and supplies this digital signal as a cuff pressure signal to the central controller 35.

The pressure change of the sub air bladder 7 is input to the pressure sensor 16 as a sub air bladder pressure detecting unit. A pressure measuring unit 17 for conversion into an analog electrical signal is connected to the pressure sensor 16, and an A/D converter 18 is connected to the pressure measuring unit 17. The A/D converter 18 outputs a digital signal as a sub cuff pressure signal to the central controller 35.

The central controller 35 includes a RAM 38 for performing, for example, read and write of measurement data and analytical results, a pulse wave processor 39 for detecting a pulse wave signal superposed on a cuff pressure signal, a cuff pressure controller 40 for pressurizing and depressurizing the compression air bladder and pulse wave detection air bladder, a sub cuff pressure controller 41 for pressurizing and depressurizing the sub air bladder, a blood pressure measuring unit 42 for determining the blood pressure from the detected pulse wave change and cuff signal, a display controller for displaying the measured blood pressure value on a liquid crystal display 37 of a blood pressure display unit, and a ROM 36 storing various readable control programs. Note that the RAM 38 also functions as a work area of programs to be processed by the central controller 35. The central controller 35 is also connected to the liquid crystal display 37 as a blood pressure display unit configured to display the blood pressure value, and drivers for performing the above-mentioned driving control operations. The central controller 35 is further connected to a battery 44 and measurement start switch 43, as shown in FIG. 1.

The blood pressure measuring apparatus configured as described above can be operated as shown in flowcharts of blood pressure measuring routines (to be described later) by the central controller 35 by reading out the various measurement control programs prestored in the ROM 36.

Figure 2A:
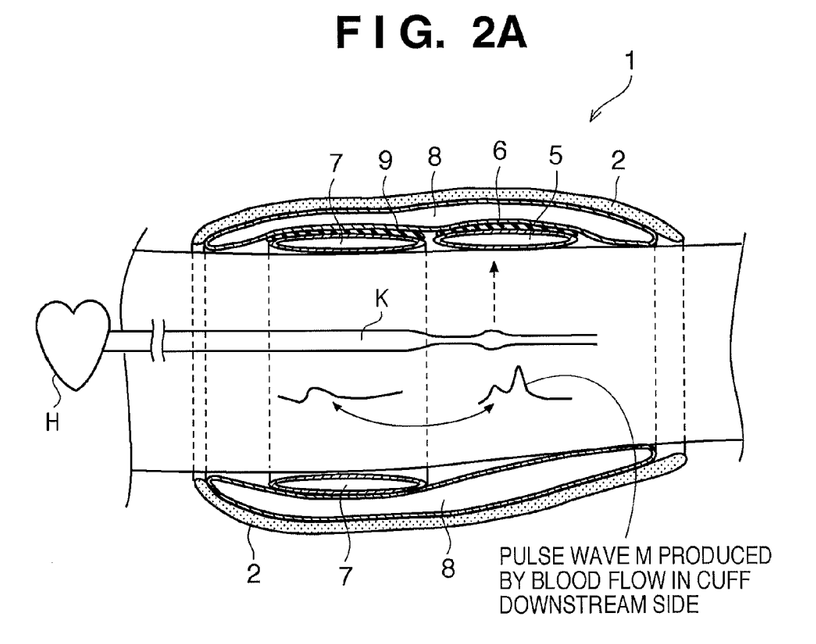
FIG. 2A is a sectional view showing the state after a cuff main body 1 is attached to the upper arm.
Figure 2B:
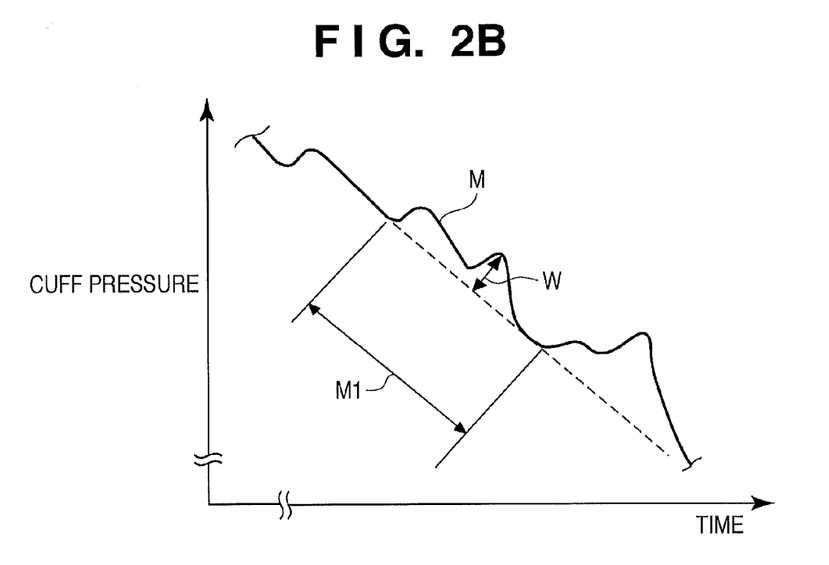
FIG. 2B is a graph showing a pulse waveform detected in a cuff depressurizing step.

FIG. 2A is a sectional view showing the state after the cuff main body 1 is attached to the upper arm. FIG. 2B is a graph showing a pulse waveform detected in a cuff depressurizing step. Note that the same reference numerals denote already explained arrangements or parts, and a repetitive explanation will be omitted. Referring to FIG. 2A, after the cuff main body 1 is attached to the upper arm, the sub air bladder 7 is positioned on the side of the heart H, and fixed to the compression air bladder 8 with the above-mentioned first damping member 9 being interposed between them. Also, the pulse wave detection air bladder 5 is positioned on an artery K in a measurement portion with the second damping member 6 being interposed, and detects a pulse wave from a blood flow generated by the pulsation of the artery K. Referring to FIG. 2B, in the cuff depressurizing step (to be described later), a pulse wave M rises once after the blood flows to the cuff edge for the first time during one heart beat M1, and the pulse wave detection air bladder detects a maximum amplitude W.

Figure 3:
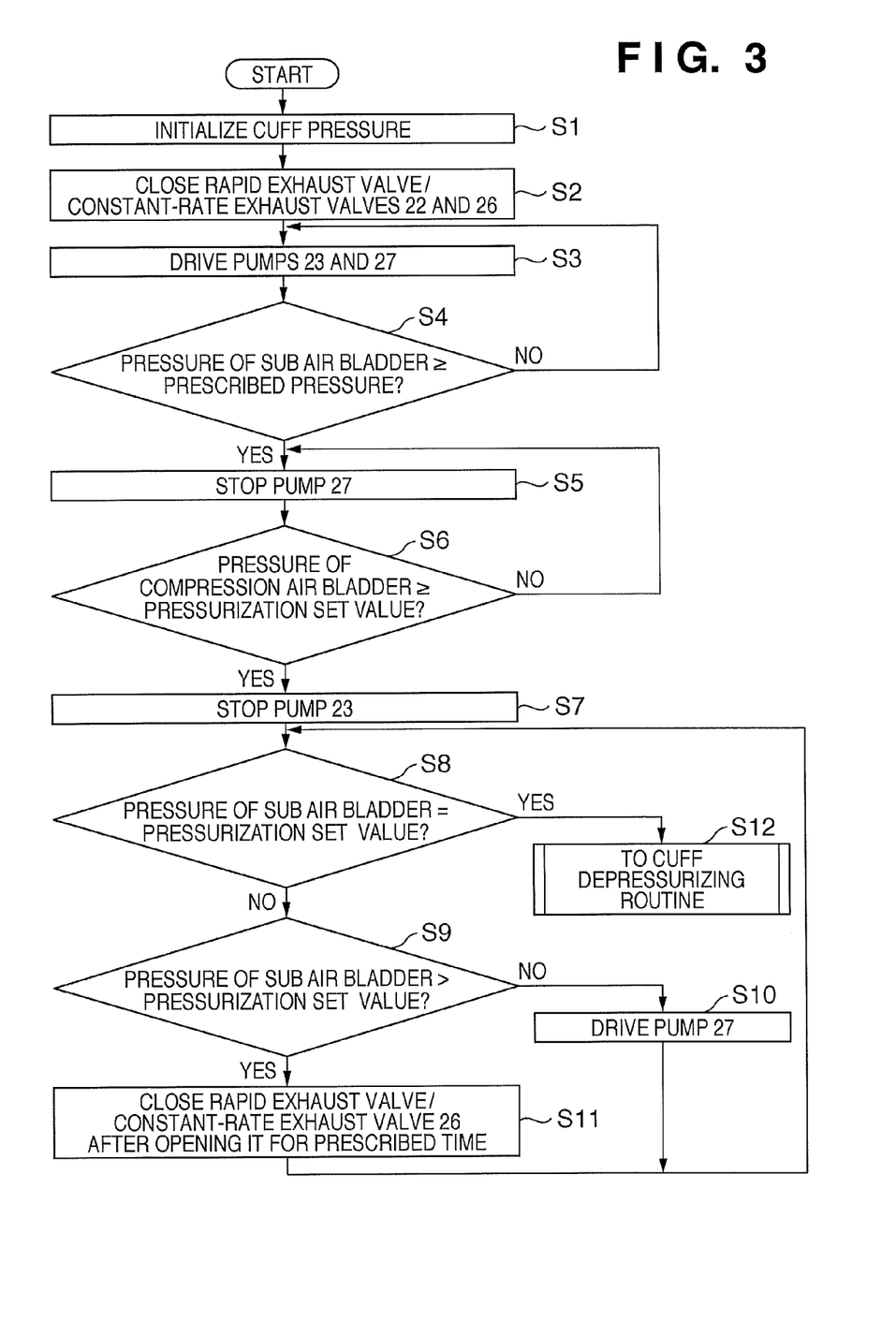
FIG. 3 is a flowchart for explaining the operation of a cuff pressurizing routine of the blood pressure measuring apparatus.

FIG. 3 is a flowchart of the cuff pressurizing routine of the blood pressure measuring apparatus configured as described above. First, the cuff main body 1 is attached to, for example, the upper arm, as shown FIG. 2. When the measurement start switch 43 is pressed after that, the air bladders are exhausted by fully opening the opening areas of the rapid exhaust valve/constant-rate exhaust valve 22 and rapid exhaust valve/constant-rate exhaust valve 26. When the residual air in each air bladder is completely exhausted in step S1 by the above operation, zero setting (initialization) is performed for the pressure sensors 31 and 16.

Subsequently, the process advances to step S2, and the rapid exhaust valve/constant-rate exhaust valve 22 and rapid exhaust valve/constant-rate exhaust valve 26 are completely closed. This makes each air bladder ready for pressurization. In step S3, electric power is supplied to the pumps 23 and 27. In step S4, whether a prescribed pressure (a pressure that does not interfere with blood flow occlusion and inflates the sub air bladder 7 so as to reduce the cuff-edge effect) is reached is checked. If the prescribed pressure is reached, the process advances to step S5 to stop the power supply to the pump 27. In this step, the pump 23 is continuously driven to set the pressure of the compression air bladder 8 at a pressurization set value higher than a predicted systolic blood pressure by 20 to 30 mmHg. In step S6, whether the pressure of the compression air bladder is equal to the pressurization set value is determined. If the pressure is equal to the pressurization set value, the driving of the pump 23 is stopped in step S7.

After that, the process advances to step S8 of adjusting the pressure of the sub air bladder 7, and the pressure of the sub air bladder 7 is checked. If the pressure of the sub air bladder 7 is not equal to that of the compression air bladder 8, the process advances to step S9. In step S9, the pressure of the sub air bladder is compared with that of the compression air bladder. If the pressure of the sub air bladder is lower than that of the compression air bladder, the process advances to step S10 to supply power to the pump 27, and the process returns to step S8. If the pressure of the sub air bladder is higher than that of the compression air bladder, the process advances to step S11 to drive the rapid exhaust valve/constant-rate exhaust valve 26. The rapid exhaust valve/constant-rate exhaust valve 26 is opened for a predetermined time and then closed, and the process returns to step S8.

When the pressure of the sub air bladder is made equal to the pressurization set value by the above control, the process advances to a depressurizing routine in step S12.

Figure 4:
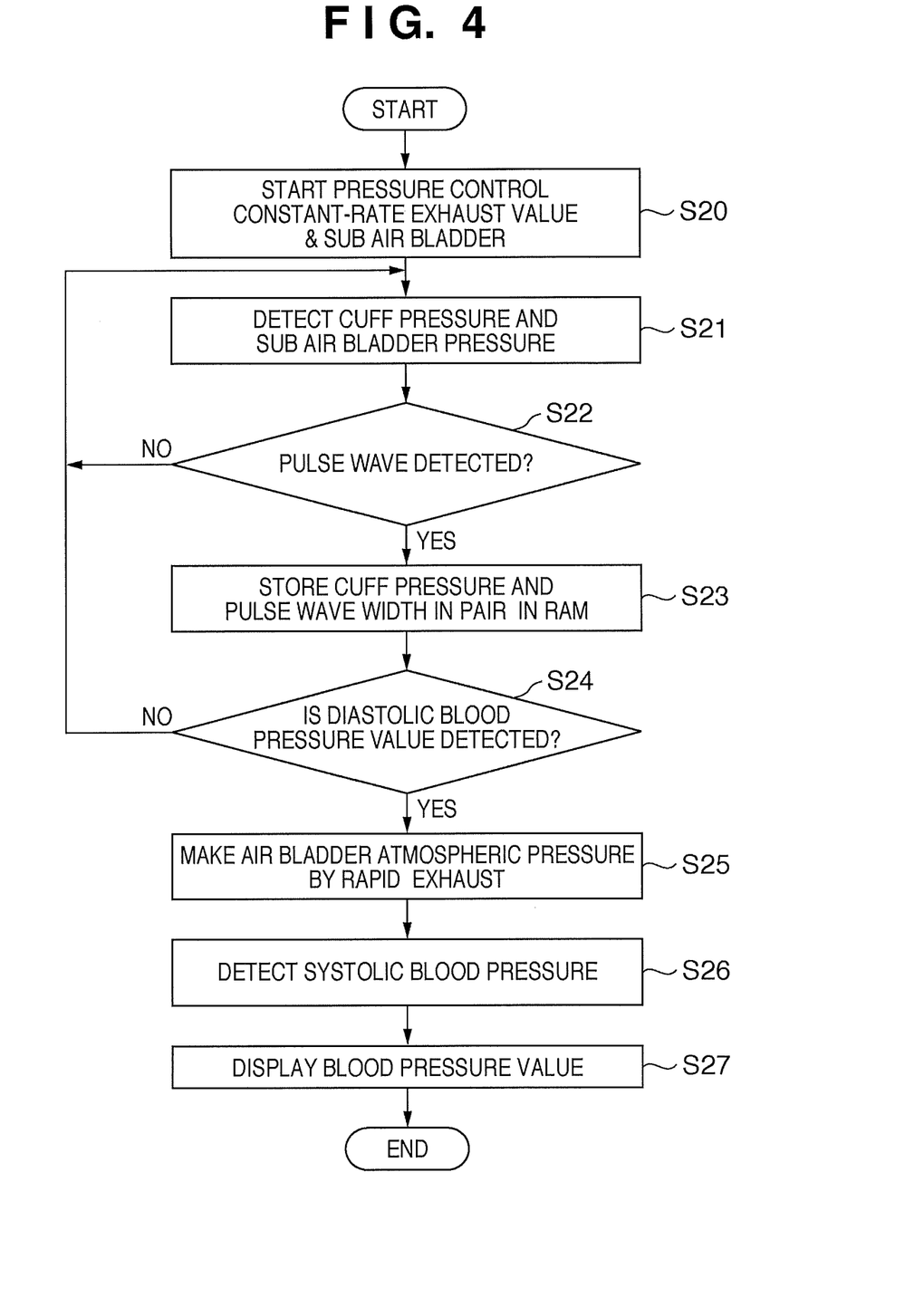
FIG. 4 is a flowchart for explaining the operation of a cuff depressurizing routine of the blood pressure measuring apparatus.

When the process advances to step S20 of the cuff depressurizing routine shown in FIG. 4, the rapid exhaust valve/constant-rate exhaust valve 22 starts constant-rate exhaustion. That is, the cuff pressure controller 40 starts constant-rate depressurization by which the opening area of the rapid exhaust valve/constant-rate exhaust valve 22 is changed such that the depressurization rate is 2 to 4 mmHg/sec, by using a signal from the cuff pressure detection unit. In synchronism with this constant-rate depressurization, the rapid exhaust valve/constant-rate exhaust valve 26 is controlled such that the pressure of the sub air bladder is equal to that of the compression air bladder. If the pressure of the sub air bladder dissociates from that of the compression air bladder, the sub cuff pressure controller 41 performs control to eliminate the dissociation by adjusting the opening area of the rapid exhaust valve/constant-rate exhaust valve 26, by using the signal from the cuff pressure detection unit. If a pulse wave change which is a changing component faster than the pressure change at a depressurization rate of 2 to 4 mmHg/sec, the sub cuff pressure controller 41 adjusts the opening area of the rapid exhaust valve/constant-rate exhaust valve 26 to cancel the pulse wave change, thereby reducing the component of the fast pressure change. The control process of adjusting the openings of the rapid exhaust valve/constant-rate exhaust valve 22 and rapid exhaust valve/constant-rate exhaust valve 26 is executed at an appropriate time by using an interrupt timer or the like independently of the process loop from step S21.

In step S21, the cuff pressure is obtained from the cuff pressure detection unit. In step S22, whether the pulse wave processor 39 has detected a pulse wave is determined. If a pulse wave is detected, the RAM 38 stores a pair of the cuff pressure and pulse wave amplitude in step S23. If the pulse wave processor 39 has not detected any pulse wave, the process returns to step S22 to loop the process until the pulse wave processor 39 detects a pulse wave.

If a phenomenon in which a pulse wave amplitude reduces every heart beat is detected in step S23, a maximum amplitude value of the pulse waves detected so far is detected. From pulse waves detected at cuff pressures lower than a cuff pressure at which a pulse wave corresponding to the maximum pulse wave amplitude value is detected, a pulse wave whose amplitude is equal to or smaller than a value obtained by multiplying the maximum pulse wave amplitude value by a predetermined ratio, for example, 60% is detected. If this pulse wave continues for three pulses, a cuff pressure at which the amplitude is 60% or less for the first time is determined as the diastolic blood pressure, and recorded as a diastolic blood pressure value in the RAM 38. The process then advances to step S25. If no cuff pressure is determined as the diastolic blood pressure, the process returns to step S22 to repeat the above processing loop until the next pulse wave is detected. After that, in step S25, the air bladders are set at the atmospheric pressure by fully opening the opening areas of the rapid exhaust valve/constant-rate exhaust valve 22 and rapid exhaust valve/constant-rate exhaust valve 26. In step S26, the time series of the pairs of pulse wave amplitudes and cuff pressures stored in the RAM 38 is called in the reverse order from the pulse wave for which the maximum pulse wave amplitude value is detected, and a point at which the pulse wave amplitude abruptly decreases by a prescribed value or more is detected. A cuff pressure corresponding to the detected point is recorded as a systolic blood pressure value in the RAM 38.

In step S27, the liquid crystal display 37 displays the systolic blood pressure value and diastolic blood pressure value stored in the RAM 38, thereby terminating the series of the blood pressure measuring operations.

Referring to FIG. 2 again, at the systolic blood pressure measurement timing, the blood vessel volume change below a cuff used by the conventional oscillometric method is about 50% of the overall blood vessel volume below the cuff, because the blood vessel in the central portion and downstream portion below the cuff is closed with pressure, and only the blood vessel on the upstream side of the central portion below the cuff is repetitively fully opened and closed with pressure. For this reason, a sphygmomanometer using the conventional oscillometric method adopts a method by which a cuff internal pressure value at the timing at which the pulse wave amplitude is about 50% of the detected maximum pulse wave amplitude is regarded as a systolic blood pressure value.

Unfortunately, this ratio is influenced by the unbalance in volume between the upstream and downstream portions, which contributes to the formation of a pulse wave below the cuff caused by the variation in blood vessel pressing force below the cuff resulting from the way the cuff is wound, the variation in relation between the cuff pressure and compliance, which is produced by the difference between cuff air amounts resulting from the cuff winding strength, and the variation in rise of the blood vessel internal pressure in a peripheral portion (the variation in reflection from the peripheral portion), which relates to the magnitude of the maximum pulse wave amplitude. Also, the rise in blood vessel internal pressure in the peripheral portion is influenced by the degree of congestion caused by the shortness of the repetition time of blood pressure measurement. These factors largely depend on the blood pressure value, the thickness of the blood vessel, the elastic characteristics, and poor peripheral circulation of a living body, and produce individual differences.

In the triple cuff, however, including the compression air bladder designed as described above and used to press the blood vessel, the pulse wave detection air bladder for detecting only a pulse wave in the central portion below the compression air bladder, and the sub air bladder for suppressing the insufficiency (cuff-edge effect) of the compression force in the cuff upstream portion, the pressure of the sub air bladder can independently be adjusted as described above. Consequently, the vibration can be extracted as a pressure signal of the sub air bladder, and the sub air bladder pressurization/depressurization control unit can control the pressure of the sub air bladder while performing feedback so as to cancel the vibration. This makes it possible to suppress the pressure signal change itself resulting from the volume change below the sub air bladder, and largely suppress the transmission of the vibration between the sub air bladder and compression air bladder. As a result, the systolic blood pressure value can be determined by performing search in ascending order of cuff pressure from the cuff pressure at which the pulse wave amplitude is maximum, and detecting a point at which the pulse wave amplitude abruptly decreases.

The present invention is not limited to the above embodiment and various changes and modifications can be made without departing from the spirit and scope of the invention. Therefore, to apprise the public of the scope of the present invention, the following claims are appended.

The invention claimed is:

1. A blood pressure measuring apparatus comprising:
   a cuff member configured to be attached to and detached from a blood pressure measurement portion;
   a cuff main body including a compression air bladder which is formed on a side of said cuff member, which is in contact with the blood pressure measurement portion, and presses the blood pressure measurement portion,
   a sub air bladder which is formed on a side of said compression air bladder, which is in contact with the blood pressure measurement portion, and presses a heart side of the blood pressure measurement portion, and
   a pulse wave detection air bladder which is formed on the side of said compression air bladder, which is in contact with the blood pressure measurement portion, and detects a pulse wave downstream of a central portion of the blood pressure measurement portion;
   a compression air bladder pressurizing/depressurizing unit configured to pressurize/depressurize said compression air bladder and said pulse wave detection air bladder;
   a sub air bladder pressurizing/depressurizing unit configured to pressurize/depressurize said sub air bladder;
   a cuff pressure detecting unit configured to obtain a cuff pressure signal from said pulse wave detection air bladder;
   a sub air bladder pressure detecting unit configured to obtain a sub air bladder pressure signal from said sub air bladder;
   a pulse wave detecting unit configured to detect a pulse wave superposed on the cuff pressure signal, and obtaining a pulse wave signal;
   a blood pressure determining unit configured to determine a blood pressure value based on the cuff pressure signal and the pulse wave signal;
   a blood pressure display unit configured to display the blood pressure value;
   a first tube connected between said pulse wave detection air bladder and said cuff pressure detecting unit;
   a second tube connected between said compression air bladder and said compression air bladder pressurizing/depressurizing unit, and connected to said cuff pressure detecting unit via a fluid resistance;
   a third tube connected between said sub air bladder and said sub air bladder pressurizing/depressurizing unit, and connected to said sub air bladder and said sub air bladder pressurizing/depressurizing unit; and
   a control unit configured to control, after said compression air bladder and said sub air bladder are pressurized by said compression air bladder pressurizing/depressurizing unit and said sub air bladder pressurizing/depressurizing unit, said compression air bladder pressurizing/depressurizing unit and said sub air bladder pressurizing/depressurizing unit so as to depressurize said compression air bladder and said sub air bladder at the same depressurization rate, and obtain the pulse wave signal.

2. The blood pressure measuring apparatus according to claim 1, wherein said control unit performs control of:
   pressurizing said sub air bladder to a prescribed pressure by said sub air bladder pressurizing/depressurizing unit, and then stopping the pressurization;
   pressurizing said compression air bladder to a pressurization target pressure higher than a systolic blood pressure by said compression air bladder pressurizing/depressurizing unit, and then stopping the pressurization; and
   determining whether the prescribed pressure of said sub air bladder differs from the pressurization target pressure, and, if the prescribed pressure differs from the pressurization target pressure, making the prescribed pressure equal to the pressurization target pressure by said sub air bladder pressurizing/depressurizing unit.

3. The blood pressure measuring apparatus according to claim 1, wherein said control unit performs control of:
   pressurizing said sub air bladder by said sub air bladder pressurizing/depressurizing unit, and stopping the pressurization after an elapse of a prescribed time;
   pressurizing said compression air bladder to a pressurization target pressure higher than a systolic blood pressure by said compression air bladder pressurizing/depressurizing unit, and then stopping the pressurization; and
   determining whether the pressure of said sub air bladder differs from the pressurization target pressure, and, if the pressure of said sub air bladder differs from the pressurization target pressure, making the pressure of said sub air bladder equal to the pressurization target pressure by said sub air bladder pressurizing/depressurizing unit.

4. The blood pressure measuring apparatus according to claim 1, wherein said control unit performs control of:
simultaneously starting pressurization by said compression air bladder pressurizing/depressurizing unit and said sub air bladder pressurizing/depressurizing unit, and stopping said sub air bladder pressurizing/depressurizing unit when said sub air bladder has reached a prescribed pressure;
pressurizing said compression air bladder to a pressurization target pressure higher than a systolic blood pressure by said compression air bladder pressurizing/depressurizing unit, and then stopping the pressurization; and
determining whether the prescribed pressure of said sub air bladder differs from the pressurization target pressure, and, if the prescribed pressure differs from the pressurization target pressure, making the prescribed pressure equal to the pressurization target pressure by said sub air bladder pressurizing/depressurizing unit.

5. The blood pressure measuring apparatus according to claim 1, wherein said control unit performs control of:
simultaneously starting pressurization by said compression air bladder pressurizing/depressurizing unit and said sub air bladder pressurizing/depressurizing unit, and stopping said sub air bladder pressurizing/depressurizing unit when said sub air bladder has reached a prescribed time;
pressurizing said compression air bladder to a pressurization target pressure higher than a systolic blood pressure by said compression air bladder pressurizing/depressurizing unit, and then stopping the pressurization; and
determining whether the prescribed pressure of said sub air bladder differs from the pressurization target pressure, and, if the pressure of said sub air bladder differs from the pressurization target pressure, making the pressure of said sub air bladder equal to the pressurization target pressure by said sub air bladder pressurizing/depressurizing unit.

6. The blood pressure measuring apparatus according to claim 1, wherein said control unit performs control of said sub air bladder pressurizing/depressurizing unit so as to cancel a pulse wave based on a blood vessel volume change detected from the pressure signal of said sub air bladder, thereby attenuating a pulse wave signal detected upstream of said pulse wave detection air bladder.

* * * * *